United States Patent [19]

Irikura et al.

[11] Patent Number: 4,559,402

[45] Date of Patent: Dec. 17, 1985

[54] PYRAZOLOPYRIDINES AND TETRAHYDRO PYRAZOLOPYRIDINES

[75] Inventors: Tsutomu Irikura, Tokyo; Seigo Suzue, Saitama; Hideo Okubo; Katsuya Awano, both of Ibaragi, all of Japan

[73] Assignee: Kyorin Seiyaki Kabushiki Kaisha, Tokyo, Japan

[21] Appl. No.: 591,381

[22] Filed: Mar. 20, 1984

[30] Foreign Application Priority Data

Mar. 26, 1983 [JP] Japan .................................. 58-51053

[51] Int. Cl.$^4$ ........................................... C07D 487/04
[52] U.S. Cl. .................................................... 546/121
[58] Field of Search .......................................... 546/121

[56] References Cited

U.S. PATENT DOCUMENTS 4,028,370 6/1977 Irikura ................................. 260/296

OTHER PUBLICATIONS

"Organic Chemistry", Robert T. Morrison and Robert Boyd, 2nd Ed., Allyn and Bacon, Inc. Boston, 1966, Sections 6.3 and 6.4.

*Primary Examiner*—Henry R. Jiles
*Assistant Examiner*—Barbara Cassatt
*Attorney, Agent, or Firm*—Toren, McGeady, Stanger, Goldberg & Kiel

[57] ABSTRACT

This invention relates to new and useful pyrazolopyridine and tetrahydro pyrazolopyridine derivatives which possess inhibitory activities on platelet aggregation. More particularly, it relates to method for their production as well as therapeutic compositions containing these compounds as used in cerebral and peripheral vascular insufficiency and its complications.

9 Claims, 1 Drawing Figure

PYRAZOLOPYRIDINES AND TETRAHYDRO PYRAZOLOPYRIDINES

BACKGROUND OF THE INVENTION

1. Field of the Invention

The present invention is concerned with certain novel pyrazolo[1,5-a]pyridine and 4,5,6,7-tetrahydropyrazolo-[1,5-a]pyridine derivatives, which have inhibitory activities on platelet aggregation and are useful for treating cerebral and peripheral vascular insufficiencies and accompanying complications containing them.

Recently, it is generally accepted that platelets and/or products of arachidonic acid metabolism have an important role in the etiology of thrombotic diseases and arteriosclerosis. Therefore, developments of much more valuable antiaggregants have been largely desired.

As a result of the intense investigation, the present investigators have now unexpectedly found that new derivatives of pyrazolo[1,5-a]pyridine and 4,5,6,7-tetrahydropyrazolo[1,5-a]pyridine possess a potent inhibitory activity on platelet aggregation. This is unobvious from the known arts of the similar series.

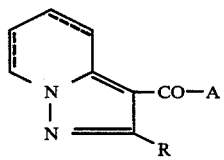

[I]

[Wherein, R is lower alkyl. A is tetrahydro-3-pyridyl which may be substituted at the N-position by lower alkyl, or $R^1$—NHCO— (wherein $R^1$ is a phenyl group which may be substituted), or 3-pyridyl group].

Thus the present compounds are useful as agents for preventing or treating, for example, cerebrovascular disease, thrombosis, migrainia, local anemic infarction, myocardial ischemia and infarction, vascular complications accompanied with cancer or diabetes, and so on.

The compounds or their salts are used in human and veterinary medicine in intact or in pharmaceutical compositions, which additionally comprise an inert physiologically acceptable carrier. For oral or parenteral administration, suitable forms of pharmaceutical composition are, for example, compressed tablets, capsules, liquors, injections, suppositories, powders, syrups and so on.

DETAILED DESCRIPTION OF THE INVENTION

Figure 1:
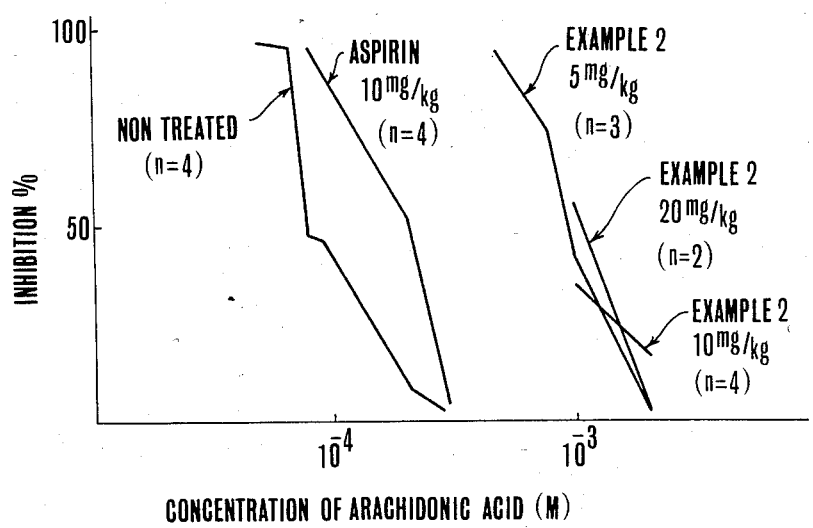
FIG. 1 shows effects of the compound of Example 2 on the arachidonic acid-induced aggregation of platelets from rabbit which had been administered orally.

The compounds of the invention can be prepared by various methods as follows:

1. Pyrazolo[1,5-a]pyridine and 4,5,6,7-tetrahydro-[1,5-a]pyridine derivatives [IV] having the general formula [I] in which A is 3-pyridyl, can be obtained by the reaction with a compound indicated by the formula [II] with a compound indicated by the formula [III] or the salt thereof,

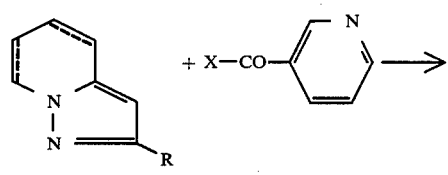

[II]  [III]

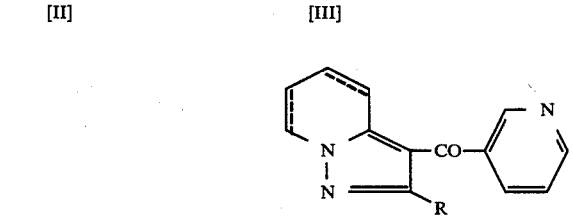

[IV]

[wherein R is defined as above defined and X means a reactive leaving group] in an appropriate solvent or in the absence of a solvent, at a temperature in the range of room temperature to near 200° C. In some cases, the addition of catalysts, such as, aluminum chloride, sulfuric acid, phosphoric acid, and so on, may be preferable. Typically, the compound can be obtained by heating a compound indicated by the formula [III] (in which X is a chlorine and which can be obtained by the reaction of the corresponding carboxylic acid and chlorinating agent, such as, thionyl chloride) with a compound indicated by the formula [II] in an appropriate solvent, such as, nitrobenzene, 1,4-dioxane, and so on, at a temperature in the range of 100° to 200° C., preferably between about 140° C. and 160° C.

2. Pyrazolo[1,5-a]pyridine and 4,5,6,7-tetrahydropyrazolo[1,5-a]pyridine derivatives[VI-b] having the general formula [I] in which A is a tetrahydro-3-pyridyl group, can be obtained by the hydrogenation of a compound indicated by the formula [V] in an appropriate solvent such as alcohol, at a hydrogen pressure, for example, in the range of 10–50 kg/cm² in the presence of appropriate catalyst such as palladium carbon. At a lower temperature (room temperature to about 60° C.), a compound indicated by the formula [VI-a] can be obtained, and at a higher temperature (above about 60° C.), a compound indicated by the formula [VI-b] can be obtained.

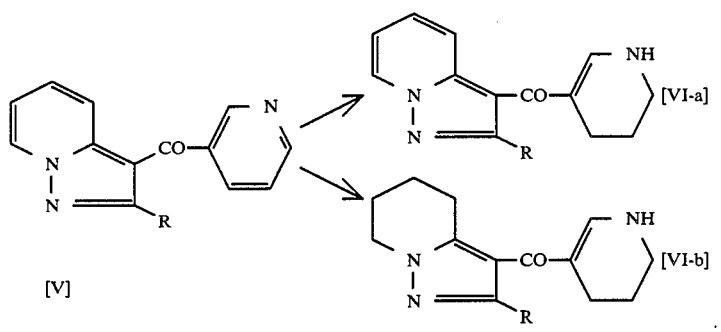

[wherein R is defined as hereinabove].

3. Pyrazolo[1,5-a]pyridine and 4,5,6,7-tetrahydro[1,5-a]pyridine derivatives [VIII] having the general formula [I], [wherein A is a tetrahydro-3-pyridyl group which is substituted at the N-position by a lower alkyl or $R^1$—NHCO—], can be obtained by the reaction of a compound of general formula [VI] with a compound of general formula [VII] in a conventionally known way. Typically, the compound [VI] is dissolved in an appropriate solvent, such as dimethylformamide, followed by addition of sodium hydride, and the resulting anion is made to react with an alkylating reagent of the general formula [VII] to afford an N-alkylated compound. In addition, a compound of the general formula [VII] in which $X^1$ is an isocyanate, reacts easily with a compound of the general formula [VI] by mixing them in methylene dichloride.

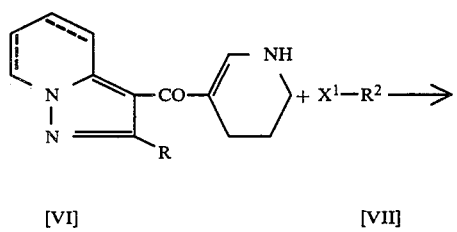

[VI]    [VII]

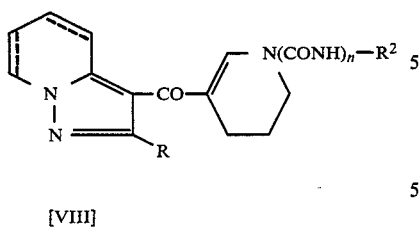

[VIII]

[Wherein $X^1$ is a nucleously convertible group, such as halogen or sulfonic acid ester, or isocyanate group, $R^2$ is a lower a phenyl group which may occasionally be substituted by halogen.]

The pharmaceutically acceptable salts of the compound of the present invention can be obtained by the reaction of a free base of the compound of the invention with a desired acid in an appropriate solvent, in the usual way.

The following examples illustrate this invention in detail, however, without restricting it thereto.

EXAMPLE 1

Preparation of 2-methyl-3-nicotinoylpyrazolo[1,5-a]pyridine

To a mixture of 107 g of nicotinic acid and 315 ml of nitrobenzene were added dropwise whilst stirring 107 g of thionyl chloride, the mixture was warmed for one hour at a temperature of 160°–180° C. The reaction mixture was allowed to cool, then 35 g of 2-methylpyrazolo[1,5-a]pyridine was introduced in one portion, and the mixture was heated to 140°–160° C. for 2 hours, and poured into 1 l of ice water. Next, 50 ml of concentrated hydrochloric acid were added. This solution was extracted twice with 500 ml of benzene. After neutralizing with potassium carbonate, the aqueous layer was extracted with chloroform, the extract was dried with anhydrous $Na_2SO_4$ and after removal of the chloroform, the residue was chromatographed over $SiO_2$ employing $CH_2Cl_2$—AcOEt (3:2) mixture as eluent. The eluate was evaporated to dryness in vacuo and the residue was recrystallized (EtOH-Hexane); yield 30 g (46%), mp 89°–90° C.

|   | C | H | N |
|---|---|---|---|
| Anal. Cald. for $C_{14}H_{10}N_3O$ | 70.87 | 4.67 | 17.71 |
| Found | 70.71 | 4.58 | 17.47 |

EXAMPLE 2

Preparation of 2-methyl-3-(1,4,5,6-tetrahydronicotinoyl)pyrazolo[1,5-a]pyridine

Ten g of 2-methyl-3-nicotinoyl pyrazolo[1,5-a]pyridine was dissolved in 150 ml of absolute ethanol and 2 g of 10% palladium carbon was added to the solution. The mixture was hydrogenated in an autoclave at 13 atm. of hydrogen at a temperature in the range of 55° to 58° C. for 3 hours. The mixture was filtered and the filtrate was evaporated under reduced pressure in order to remove the solvent. The residue was recrystallized from ethyl acetate to afford the title compound in yield of 8.5 g, mp 207°–208° C.

|   | C | H | N |
|---|---|---|---|
| Anal. Cald. for $C_{14}H_{15}N_3O$ | 69.69 | 6.27 | 17.42 |
| Found | 69.78 | 6.27 | 17.31 |

EXAMPLE 3

Preparation of 2-methyl-3-(1,4,5,6-tetrahydronicotinoyl)-4,5,6,7-tetrahydropyrazole[1,5-a]pyridine By following the procedure of Example 2, it was hydrogenated at 15 atm. and at 80° C., and recrystallized from ethyl acetate to afford the title compound in yield of 30 g (74%), mp 135°–136° C.

|  | C | H | N |
|---|---|---|---|
| Anal. Cald. for $C_{14}H_{19}N_3O$ | 68.54 | 7.81 | 17.13 |
| Found | 68.35 | 7.81 | 16.98 |

EXAMPLE 4

Preparation of 2-methyl-3-[1-(p-chlorophenylcarbamoyl)-1,4,5,6-tetrahydronicotinoyl]-pyrazolo[1,5-a]pyridine One g of 2-methyl-3-(1,4,5,6-tetrahydronicotinoyl)-pyrazolo[1,5-a]pyridine was dissolved in 20 ml of methylene chloride and 1 g of p-chlorophenyl isocyanate was added dropwise whilst stirring to the solution. The mixture was stirred at room temperature for 2 hours, and after removal of solvent in vacuo, the residue was recrystallized from ethyl acetate to afford the title compound in yield of 1.2 g (73%), mp 198°–200° C.

|  | C | H | N |
|---|---|---|---|
| Anal. Cald. for $C_{21}H_{19}N_4O_2Cl$ | 63.88 | 4.85 | 14.19 |
| Found | 63.89 | 4.84 | 14.19 |

EXAMPLE 5

Preparation of 2-methyl-3-(1-ethyl-1,4,5,6-tetrahydronicotinoyl)-pyrazolo[1,5-a]pyridine One g of 2-methyl-3-(1,4,5,6-tetrahydronicotinoyl)-pyrazolo[1,5-a]pyridine was dissolved in 20 ml of dimethyl-formamide and 0.3 g of sodium hydride (55%) was added whilst stirring to the mixture. The mixture was stirred at room temperature for 1 hour, and then 1 g of ethylchloride was added and stirred at 60° C. for 2 hours. After removal of solvent in vacuo, the residue was chromatographed over $SiO_2$ employing $CH_2Cl_2$—ethyl acetate—methanol (8:1.5:0.5) mixture as eluent. The eluate was evaporated to dryness in vacuo and the residue was recrystallized from benzene-hexane to afford the title compound in yield of 0.8 g (72%), mp. 104°–105° C.

|  | C | H | N |
|---|---|---|---|
| Anal. Cald. for $C_{16}H_{19}N_3O$ | 71.34 | 7.11 | 15.60 |
| Found | 71.05 | 7.09 | 15.42 |

EXAMPLE 6

Preparation of 2-isopropyl-3-(1,4,5,6-tetrahydronicotinoyl)-pyrazolo[1,5-a]pyridine It was prepared following the procedure of Example 2, and recrystallized from ethyl acetate to afford the title compound in yield of 66%, mp. 186°–188° C.

|  | C | H | N |
|---|---|---|---|
| Anal. Cald. for $C_{16}H_{19}N_3O$ | 71.34 | 7.11 | 15.72 |
| Found | 71.33 | 7.14 | 15.55 |

EXAMPLE 7

Preparation of 2-isopropyl-3-nicotinoyl-4,5,6,7-tetrahydropyrazolo[1,5-a]pyridine It was prepared following the procedure of Example 1, and obtained as oily product in yield 41%, Mass, m/e 269 (M+).

EXAMPLE 8

Preparation of 2-isopropyl-3-(1,4,5,6-tetrahydronicotinoyl)-4,5,6,7-tetrahydropyrazolo[1,5-a]pyridine It was prepared following the procedure of Example 3, and recrystallized from benzene-hexane to afford the title compound in yield of 11%, mp. 123°–125° C.

|  | C | H | N |
|---|---|---|---|
| Anal. Cald. for $C_{16}H_{23}N_3O$ | 70.29 | 8.48 | 15.37 |
| Found | 70.03 | 8.44 | 15.21 |

EXAMPLE 9

Preparation of 2-methyl-3-nicotinoylpyrazolo[1,5-a]pyridine

To a solution of 110 g of 2-methylpyrazolo[1,5-a]pyridine in 600 ml of 1,4-dioxane was added 150 g of nicotinyl chloride hydrochloride with stirring. The resulting solution was heated to reflux for 2 hours, and after removal of solvent in vacuo, the residue was dissolved in 500 ml of water and neutralized with potassium carbonate. The aqueous layer was extracted with 500 ml of benzene, the extract was dried over anhydrous $Na_2SO_4$, and after removal of solvent, the residue was recrystallized from ethyl acetate-hexane to afford 110 g of the title compound. Concentrating the mother liquors gave a second crop of crystals, which weighed 10 g; total yield 120 g (61%), mp 89°–90° C.

|  | C | H | N |
|---|---|---|---|
| Anal. Calcd. for $C_{14}H_{10}N_3O$ | 70.87 | 4.67 | 17.71 |
| Found | 70.91 | 4.67 | 17.68 |

EXAMPLE 10

Preparation of 3-[1-(1-ethoxycarbonylethyl)-1,4,5,6-tetrahydronicotinoyl]-2-methylpyrazolo-[1,5-a]pyridine It was prepared following the procedure of Example 5, and recrystallized from ethyl acetate-hexane to afford the title compound in yield of 60%, mp. 107°–108° C.

|  | C | H | N |
|---|---|---|---|
| Anal. Cald. for $C_{19}H_{23}N_3O_3$ | 66.84 | 6.79 | 12.31 |
| Found | 66.76 | 6.89 | 12.19 |

The experiments to prove usefulness of the compounds of this invention are detailed as follows.

EXPERIMENT 1

In vitro studies on platelet aggregation

The antiaggregant activity in vitro of the present compounds was studied in platelet rich plasma from rabbit and man.

(A) Effects on rabbit platelet aggregation

Blood was taken from the femoral artery of rabbit with a syringe containing sodium citrate (3.8%, 1 vol. in 9 vol. of blood). The citrated blood was centrifuged at 800 rpm. The supernatants were stored at 10° C. until use as platelet rich plasma (PRP) in the subsequent experiment. Platelet aggregation was determined with aggregometer (D-P 247 E, SIENCO Ltd.). Stock solution of test compounds was made by suspending at a concentration of 10 mg/ml in 1% gum arabic solution. Further, dilution was made with 0.9% saline. PRP was preincubated for 3 min. with the test compounds, and then arachidonic acid as aggregant was added at final concentration of $10^{-4}$M.

The antiaggregant activities of the compounds are shown in Table 1. $IC_{100}$-values are the concentrations which gave maximum (100%) inhibition against platelet aggregation caused by arachidonic acid.

(B) Effects on human platelet aggregation

Blood samples were taken from median cubital vein of 5 healthy volunteers (male, 30 to 42 age) with plastic syringe. The citrated blood (sodium citrate 1 vol. in 9 vol. of blood) was centrifuged at 1000 rpm. The supernatant (PRP) was stored at 10° C. and used within 5 hours. Arachidonic acid ($4-8 \times 10^{-4}$M) and collagen (6-8 μg/ml, SIGMA, Type III) were used as aggregants. Other procedures were the same as in Experiment 1.

The results of this experiment show that the compound of Example 2 has potency and almost the same inhibitory activity against both arachidonic acid- and collagen-induced platelet aggregation. $IC_{100}$-values of this compound are in the range of $10^{-10}$ to $3 \times 10^{-8}$ g/ml. About 300-folds difference in the $IC_{100}$-values is considered to be due to individual difference.

On the other hand, a reference drug, aspirin, completely inhibited both arachidonic acid- and collagen-induced platelet aggregation only at concentration as high as $6-8 \times 10^{-6}$ g/ml and $10^{-4}$ g/ml, respectively.

EXPERIMENT 2

Ex vivo studies on platelet aggregation

To know the absorbability and potency of the compound of this invention, another platelet aggregation tests were done using the PRP from rabbit which had been administered orally with the drugs.

Rabbits were administered orally with the compound of Example 2 or aspirin. One hour after the drug administration, blood was taken from the femoral artery. The methods for preparing PRP and determining platelet aggregation were the same as Experiment 1. The results given in FIG. 1 indicate that the compound of Example 2 has potent inhibitory activity several times as high as aspirin on arachidonic acid-induced platelet aggregation.

EXPERIMENT 3

Effect on blood viscosity

Male Wistar rats weighing 300–380 g were used in this experiment. Rats were administered orally 10 mg/kg twice a day of the compound of Example 2 for 2 days. One hour after the last treatment, rats were anaesthetized with pentobarbital 35 mg/kg ip, and then blood was taken from vena cava caudalis. EDTA was added at a final concentration of 2 mM.

Whole blood and plasma viscosities were measured with rotational viscometer (Contraves LS-30, shear rate 0–128.5 sec.$^{-1}$, 37° C.) and hematocrit was determined by microhematocrit centrifugation (13,000 g for 5 min.).

As shown in Table 2, whole blood viscosities at shear rate 0.1285, 0.514, 6.425, 25.7 and 128.5 sec.$^{-1}$ were reduced by 50.1, 36.1, 23.5, 19.2 and 12.0%, respectively, but no effects on plasma viscosity and hematocrit were observed.

EXPERIMENT 4

Gastro-intestinal lesions in rats

Male Wistar rats weighing 250 to 300 g were used in this experiment. Ulcer formation under the satiety condition was studied as follows: Rats not fasted prior to experiment were administered orally with test compounds. The animals were allowed free access to diet and water for 24 hours after the drug administration until sacrificed by exsanguination. The stomach and the intestine were removed and examined for lesions.

In the other study, rats had been deprived of food and water for 24 hours before drug administration. The animals were administered orally with the compound of Example 2 and aspirin and then they had free access to water but not to diet. Twenty-four hours later, the animals were killed by the exsanguination. The stomach and the intestine were removed and observed carefully to know whether or not lesions were present.

As shown in Table 3, the ulcerogenic activity of the compounds is ¼ to 1/10 of that of aspirin.

EXPERIMENT 5

Acute Toxicity ($LD_{50}$)

Acute toxicity of the compound of Example 2 on Wistar rats and ICR mice are shown in Table 4.

TABLE 1

Effects of the Compounds on Rabbit Platelet Aggregation Induced by Arachidonic Acid

| Example No. | $IC_{100}$ (g/ml) |
|---|---|
| 1 | $6 \times 10^{-6}$ |
| 2 | $3 \times 10^{-8}$ |
| 3 | $2 \times 10^{-7}$ |
| 4 | $1 \times 10^{-6}$ |
| 10 | $3 \times 10^{-7}$ |
| Aspirin | $4 \times 10^{-6}$ |

TABLE 2

Effects of the Compound of Example 2 on Blood Viscosities and Hematocrits in Rats

| Shear Rate (sec.$^{-1}$) | Vehicle | Example 2 |
|---|---|---|
| | Whole Blood Viscosity (mPS) | |
| 0.1285 | 49.7 ± 6.47 | 24.8 ± 2.71* |
| 0.514 | 26.9 ± 2.08 | 17.2 ± 1.31* |
| 6.425 | 9.55 ± 0.56 | 7.31 ± 0.36* |
| 25.7 | 6.41 ± 0.25 | 5.18 ± 0.12* |
| 128.5 | 4.18 ± 0.09 | 3.68 ± 0.08* |

TABLE 2-continued

Effects of the Compound of Example 2 on Blood Viscosities and Hematocrits in Rats

| Shear Rate (sec.$^{-1}$) | Vehicle | Example 2 |
|---|---|---|
| | Plasma Viscosity (mPS) | |
| | 1.15 ± 0.01 | 1.14 ± 0.01 |
| | Hematocrit (%) | |
| | 46.1 ± 1.15 | 46.0 ± 0.71 |

*Significant difference from vehicle, $p < 0.05$ (Wilcoxon's rank sum test)

TABLE 3

Ulcerogenic Activity of the Compounds

| | Example 2 | Aspirin |
|---|---|---|
| Satiety | >1000 | 230 |
| Fasting | 300 < UD$_{50}$ < 500 | 25 < UD$_{50}$ < 50 |

Units for the UD$_{50}$-values: mg/kg, p.o. UD$_{50}$ means the dose that cause the lesions in 50% of animals.

TABLE 4

Acute Toxicity of Example 2

| | MICE | RATS |
|---|---|---|
| P.O. (mg/kg) | >1000 | >1000 |
| I.V. (mg/kg) | 125 < LD$_{50}$ < 150 | >100 |

What we claim:

1. A compound having the formula,

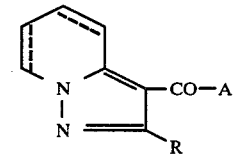

[I]

wherein

R is a lower alkyl containing 1 to 3 carbon atoms,

A is 3-pyridyl group or tetrahydro-3-pyridyl which may be substituted at the N-position by either a lower alkyl containing 1 to 2 carbon atoms, or $R^1$—NHCO— wherein $R^1$ is a phenyl group or a phenyl group substituted by halogen.

2. 2-Methyl-3-nicotinoylpyrazolo[1,5-a]pyridine.

3. 2-Methyl-3-(1,4,5,6-tetrahydronicotinoyl)-pyrazolo[1,5-a]pyridine.

4. 2-Methyl-3-(1,4,5,6-tetrahydronicotinoyl)-4,5,6,7-tetrahydropyrazolo[1,5-a]pyridine.

5. 2-Methyl-3-[1-(p-chlorophenylcarbamoyl)-1,4,5,6-tetrahydronicotinoyl]pyrazolo[1,5-a]pyridine.

6. 2-Methyl-3-(1-ethyl-1,4,5,6-tetrahydronicotinoyl)-pyrazolo[1,5-a]pyridine.

7. 2-Isopropyl-3-(1,4,5,6-tetrahydronicotinoyl)-pyrazolo[1,5-a]pyridine.

8. 2-Isopropyl-3-(nicotinoyl)-4,5,6,7-tetrahydropyrazolo[1,5-a]pyridine.

9. 2-Isopropyl-3-(1,4,5,6-tetrahydronicotinoyl)-4,5,6,7-tetrahydropyrazolo[1,5-a]pyridine.

* * * * *